United States Patent [19]

Grimberg

[11] Patent Number: 5,667,802
[45] Date of Patent: Sep. 16, 1997

[54] ANTACID COMPOSITION

[76] Inventor: Georges Serge Grimberg, 127 rue de l'Université, Paris, France, 75007

[21] Appl. No.: 441,294

[22] Filed: May 15, 1995

[30]     Foreign Application Priority Data

May 17, 1994 [FR] France ................. 94 05990

[51] Int. Cl.$^6$ ............................................. A61K 9/20
[52] U.S. Cl. ................ 424/464; 424/441; 424/48; 424/485; 424/440
[58] Field of Search ................ 424/464, 48, 440, 424/441; 426/5

[56]                References Cited

U.S. PATENT DOCUMENTS

| 3,382,150 | 5/1968 | Grass | 424/465 |
| 4,327,077 | 4/1982 | Puglia et al. | 424/38 |
| 4,764,374 | 8/1988 | Grimberg | 424/128 |
| 4,867,989 | 9/1989 | Silva et al. | 426/5 |
| 5,173,305 | 12/1992 | Grimberg | 424/682 |
| 5,288,507 | 2/1994 | Sims et al. | 424/682 |

FOREIGN PATENT DOCUMENTS

| 2578423 | 9/1986 | France . |
| 2699074 | 6/1994 | France . |

*Primary Examiner*—Thurman K. Page
*Assistant Examiner*—William E. Benston, Jr.
*Attorney, Agent, or Firm*—Browdy and Neimark

[57]            ABSTRACT

Antacids comprise a pharmaceutically acceptable gum coated with simethicone and a pharmaceutically acceptable antacid to provide prolonged antacid treatment to the stomach while preventing acid rebound. Compatible active ingredients can be included in the antacids, including analgesics, antibiotics, gold salts, and fluorine compounds.

7 Claims, 13 Drawing Sheets

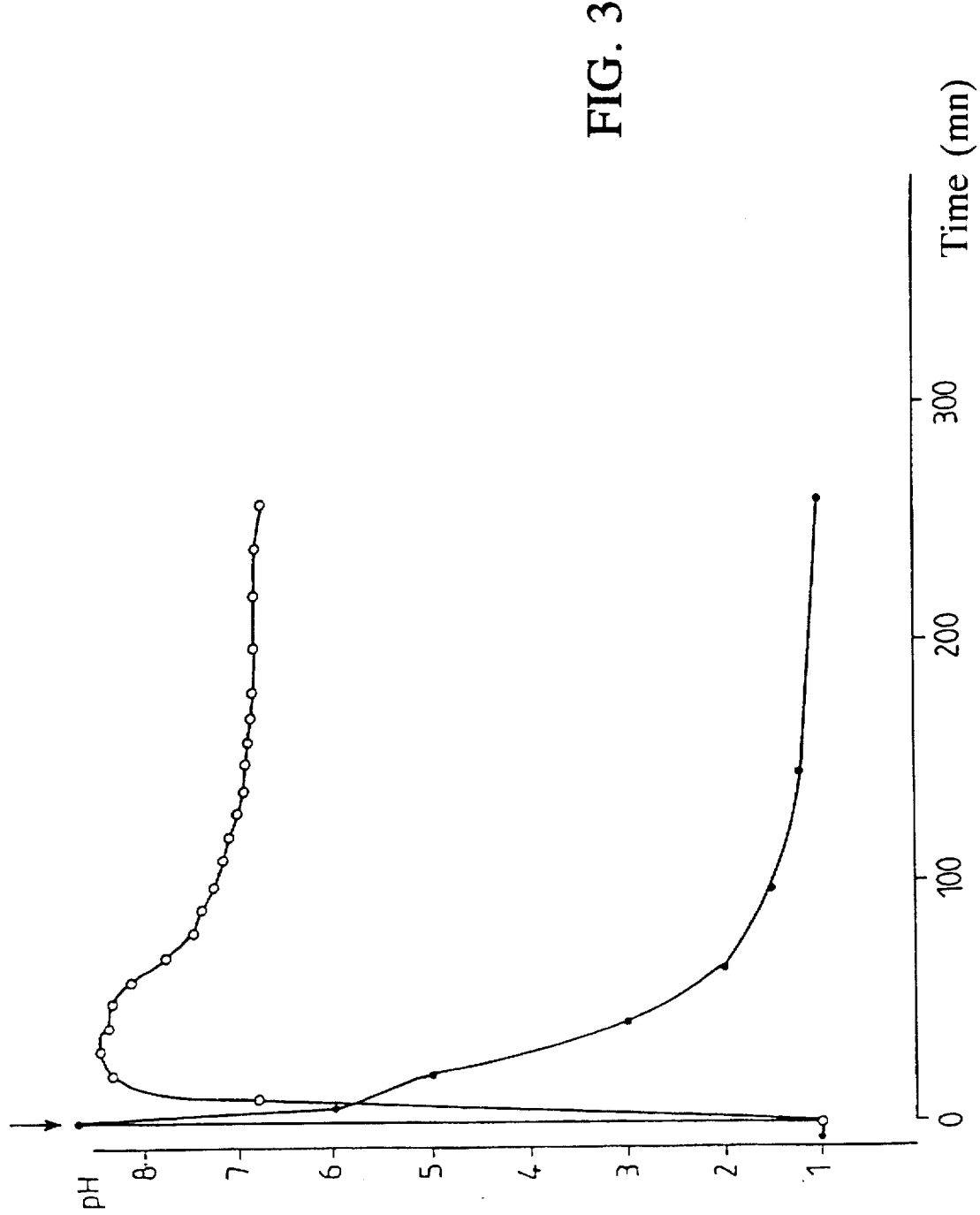

ANTACID COMPOSITION

FIELD OF THE INVENTION

The present invention relates to a pharmaceutical composition based on a simethicone-coated gum and a neutralizing antacid to which a therapeutically active substance can be added.

BACKGROUND OF THE INVENTION

Antacids have been used for generations to treat excess stomach acidity. Unfortunately, while many basic salts, such as sodium bicarbonate, offer prompt relief of acid indigestion, many of these basic compounds have the disadvantage of causing "acid rebound." In other words, because these salts have such a high pH, they overcompensate for the excess stomach acid and raise the pH of the stomach to too high a level. To overcome this increased pH, then, the stomach secretes even more acid—the acid rebound effect. This acid rebound, of course, negates the effect of the antacid, and the vicious cycle resumes.

In an effort to avoid acid rebound, many have switched to antacids based upon aluminum salts such as aluminum hydroxide. However, aluminum has now been associated with a variety of other problems, such as Alzheimer's disease and possible renal failure, so that it is now desirable to avoid ingesting antacids containing aluminum salts.

Additionally, conventional antacids are often fast acting but have no lasting effect. In other words, these compositions provided quick relief which was not sustained over a period of several hours, resulting in the need to ingest additional quantities of antacid salts.

Guar gum has been used as an antacid, as disclosed in U.S. Pat. No. 4,764,374, which corresponds to French A-2 578 423, the entire contents of which are hereby incorporated by reference.

SUMMARY OF THE INVENTION

It is an object of the present invention to avoid the aforementioned deficiencies associated with the prior art.

It is an object of the present invention to provide an improved antacid based upon a gum.

It has now been discovered upon studying neutralizing antacids that, when conventional neutralizing antacid compounds are associated with a gum coated with simethicone, there is obtained a remarkable antacid activity which lasts for a prolonged period of time.

The antacid activity of three preparations based on guar gum coated with simethicone and a magnesium salt shows that guar gum exhibits a synergistic antacid activity when combined with conventional antacid salts, in contrast with a control solution without guar gum.

In preparing compositions according to the present invention, the quantity of gum in the composition used should be enough to provide a suspension viscous enough to adhere to the oesogastroduodenal lining and be slowly diluted in the oesogastroduodenal secretions to provide a very slow release of active ingredients.

The gum is coated with simethicone, along with sufficient sorbitan monooleate, and Polysorbate 80® (polyoxyethylene 20 sorbitan monooleate) to aid in coating the gum. However, other pharmaceutically acceptable surfactants can be used in combination with the simethicone to aid in coating the gum with simethicone. The combination of coated gum and alkaline antacid salt is generally in the amount of about 0.2 g gum for 15 to 20 ml of water to form a suspension. For one tablet or one dose of powder, up to 1 gram of gum may be used.

Any complementary therapeutically active substance, which is physically compatible with the gum and antacid salt, can be incorporated in the compositions according to the present invention. Among these complementary therapeutically active substances are fluorine compounds, gold salts, acetyl salicylic acid, antibiotics, antiseptics, and anticoagulants.

While guar gum is the preferred gum for use in the compositions according to the present invention, any pharmaceutically acceptable gum which has the same viscosity-imparting characteristics and adherent properties can be used.

BRIEF DESCRIPTION OF THE DRAWINGS

FIG. 3 shows the change in pH with magnesium oxide and guar gum at an emptying time of 1.5 ml/minute.

DETAILED DESCRIPTION OF THE INVENTION

Figure 1:
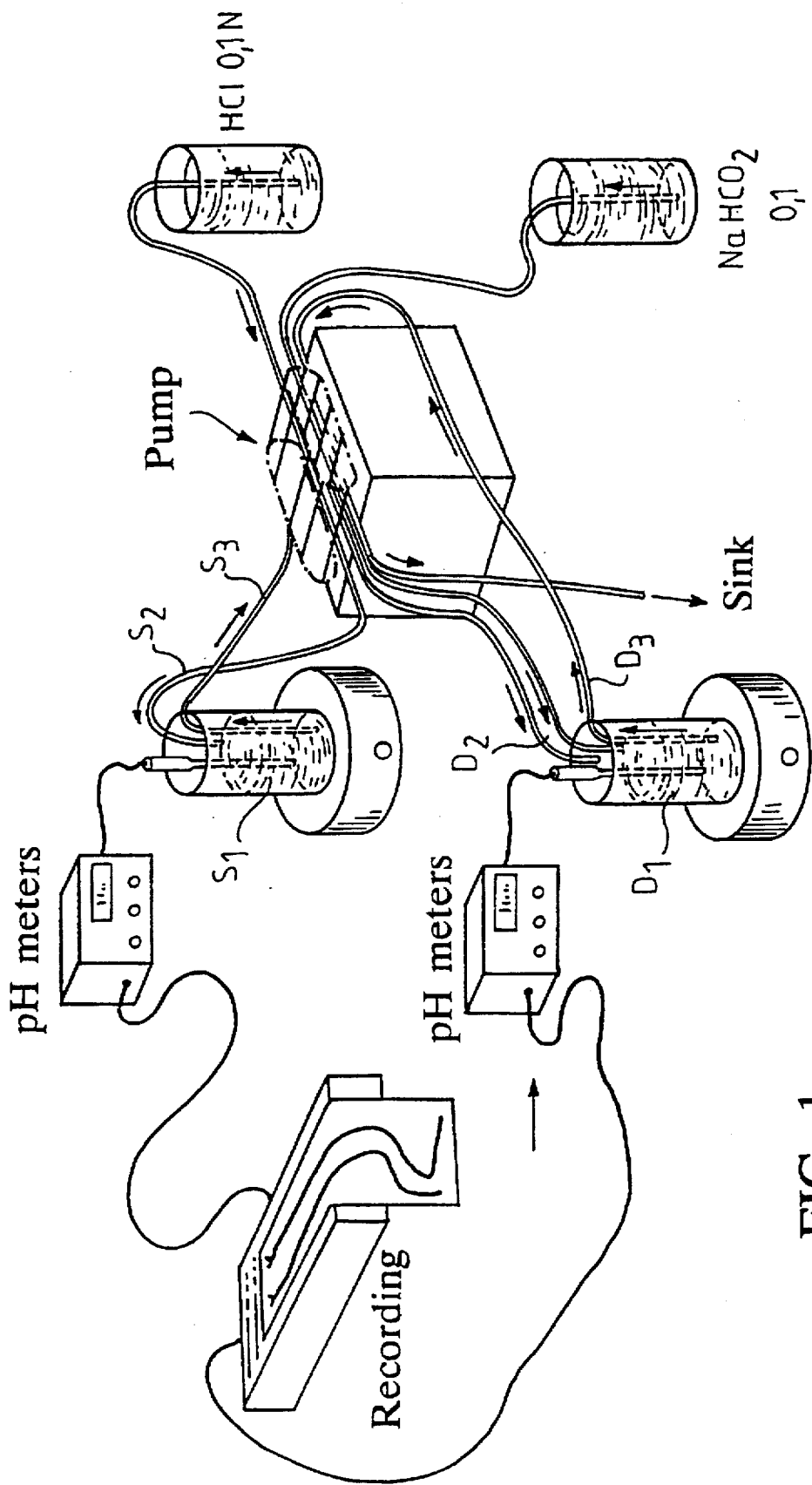
FIG. 1 represents a model of an artificial stomach-duodenum.

The compositions of the present invention comprise a gum coated with simethicone, a neutralizing antacid salt, and an optional compatible pharmaceutically active ingredient. The gum is present in the composition to provide a suspension which is sufficiently viscous to adhere to the oesogastroduodenal lining, generally from about 0.1 gram to about 1.5 gram per dose, depending upon the individual gum used and whether the composition is in suspension form or in dry (powder or tablet) form. The coating for the gum, simethicone, which may be mixed with surfactants such as sorbitan monooleate, and Polysorbate 80®, for ease of formulation, is present in sufficient quantity to envelop the gum particles. The antacid salts are in quantities sufficient to provide acceptable antacid action to a patient in need thereof. These amounts are readily determined by one skilled in the art without undue experimentation.

The term "gums" has been used to denote a wide range of compounds including polysaccharides, terpenes, proteins, and synthetic polymers. Presently, the term more specifically denotes a group of industrially useful polysaccharides or their derivatives that hydrate in hot or cold water to form viscous solutions, dispersions, or gels.

Gums are classified as natural or modified. Natural gums include seaweed extracts, plant exudates, gums from seeds or roots, and gums obtained by microbial fermentation. Modified (semisynthetic) gums include cellulose and starch derivatives as well as certain synthetic gums such as low methoxyl pectin, propylene glycol alginate, and carboxymethyl and hydroxypropyl guar gum.

Guar gum is the ground endosperms of *Cyamopsis tetragonolobus* which is cultivated in India as livestock feed. Guar gum has been used as a source of fiber in patients with non-insulin dependent diabetes (McIvor et al., *Am. J. Clin. Nutr.* 41:891, 1985), and is in the form of a free-flowing powder. Guar gum is completely soluble in both cold and hot water. Aqueous solutions of guar gum are tasteless, odorless, and nontoxic. Guar gum has five to eight times the thickening power of starch. Guar gum has historically been used in paper sizing, as a protective colloid, stabilizer, thickening, and film forming agent for cheese, salad dressings, ice cream, and soups; as a binding and disintegrating agent in tablet formulations; in pharmaceutical jelly formulations; in suspensions, emulsions, lotions, creams, and toothpastes; in the mining industry as a flocculent and as a filtering agent; and in water treatment as a coagulation aid.

Structurally, guar gum comprises a straight chain of D-mannose with a D-galactose side chain on approximately every other mannose unit; the ratio of mannose to galactose is 2:1. Guar gum has a molecular weight on the order of 220,000.

Guar gum hydrates in either cold or hot water to produce high viscosity solutions. Although the viscosity development depends upon the particle size of the guar gum, pH and temperature, a 1% solution of guar gum fully hydrates within about 24 hours at room temperature, and in about 10 minutes at 80° C. Guar gum solutions are stable over a pH range of 4.0–10.5, with the fastest hydration occurring at pH 8.0.

Among the gums that can be used in the present invention are pharmaceutically acceptable gums such as agar, algin, carrageenan, guar gum, locust bean gum, gum arabic, gum tragacanth, pectin, dextran, xanthan gum, gellan gum, karaya gum, and the like. This list is not meant to be exhaustive, but is merely illustrative of the types of pharmaceutically acceptable gums that can be used in the compositions according to the present invention. One skilled in the art can readily determined what other pharmaceutically acceptable gums can be used in these compositions, without undue experimentation. Of these gums, guar gum is the preferred.

The gum particles are coated with simethicone before being mixed with the antacid salts. Generally, the ratio of simethicone is from about 10:1 to about 1:10 by weight. To coat the gum, the simethicone is mixed with at least one surfactant/emulsifier such as sorbitan monooleate or Polysorbate 80® gum is added to the mixture and dried. Alternative methods of coating the gum with simethicone are readily apparent to one skilled in the art, and can be effected without undue experimentation.

The antacid used in the compositions according to the present invention can be any conventional, pharmaceutically acceptable antacid salt, including pharmaceutically acceptable salts of magnesium, calcium, and the like. Although aluminum has been used as an antacid salt because its salts are not as basic as most calcium and magnesium antacid salts, and thus does not cause acid rebound, aluminum has been suspected of being somewhat toxic. For example, there is a suspicion that ingestion of aluminum salts can lead to renal failure. Examples of salts for use in the compositions of the present invention include magnesium hydroxide, magnesium oxide, calcium oxide, calcium carbonate, as well as any other salts, oxides, and hydroxides which are therapeutically active for protecting the oesogastroduodenal mucous membrane. Other useful antacids can be readily identified by one skilled in the art, using the Fortran test, without undue experimentation.

The antacids can be used in quantities which are generally accepted dosages of antacids. Generally, a single dose of antacid ranges from about 0.1 gram to about 2 grams per dose. One skilled in the art can readily determine what is a useful, efficacious dose of antacid. The compositions can be administered as needed, generally about three times a day.

Complementary therapeutically active substances which can be included in the compositions according to the present invention include analgesics such as acetaminophen, aspirin, ibuprofen and other non-steroidal anti-inflammatories; gold salts used for treating arthritis; fluorine derivatives; anticoagulants, such as coumarin; and antibiotics, such as penicillin, gramicidin, tyrocidine, griseofulvin, streptomycin, polymyxin, cephalosporin, oxytetracycline, ampicillin, cephalothin, lincomycin, gentamicin, carbenicillin, cephalexin, clindamycin, and the like. This list of antibiotics is not exhaustive, but is presented to illustrate antibiotics that can be incorporated in the compositions according to the present invention. One skilled in the art can readily determine other antibiotics which can be incorporated in the compositions of the present invention. The complementary active substances are generally present in amounts ranging from about 1 mg to about 2 grams, depending upon the substance used.

To ease the understanding of the invention, the Figure represents schematically a model of an artificial stomach-duodenum. In FIG. 1, the artificial stomach-duodenum includes two pH meters 1 and 2 in connection with a recording device E1 and with container S1 which represents gastric contents; container S2 represents constant gastric secretion flow at 3 ml/minute (HCl, 0.1 Normal). S3 represents a variable gastric emptying flow of 1.5; 3.0 or 4.5 ml/minute. D1 is a container which represents the contents of the duodenum. D2 represents gastric draining flow coming into D1. D3 represents the draining flow of D1 installed, while D1 remains constant. All flows are regulated by pump P.

The pH meters and the recording with two ducts describe the registration system of gastric pH and duodenum D1.

Studies were conducted on the following compositions:

| MGO GUM 001 | |
|---|---|
| Magnesium oxide | 0.5 g |
| Coated guar gum* | 1.0 g |
| MGO GOM 001 | |
| Magnesium hydroxide | 1 gram |
| Coated guar gum | 1 gram |
| MGOH GOM 002 | |
| Magnesium hydroxide | 0.5 gram |
| Coated guar gum | |

*In all of the tests which in included coated guar gum, the guar gum was coated with approximately equal amounts of simethicone in quantity sufficient to coat the individual particles of guar gum.

The results obtained during these tests were remarkable, and presented for the first time modification of neutralizing action of the antacid salt.

The results obtained were as follows:

MGO GUM 001

Table I groups the characteristics in both a gastric and a duodenal environment after addition of a packet of MGO GUM 001 in 100 ml of HCl, 0.1N:

TABLE I

| Flow of gastric draining (ml/min) | 1.5 | 3.0 | 4.5 |
|---|---|---|---|
| Gastric environment | | | |
| maximum pH | 3.25 | 1.9 | 4.2 |
| Time (min) to reach pH 1,0 | 132 | 105 | 75 |
| Millimoles of acid used to reach pH 1,0 | 49.6 | 41.5 | 32.5 |
| Duodenal environment | | | |
| Acid charge in the duodenum (mmol) | 18.3 | 25.72 | 24.9 |
| "Alkaline secretion" mmol | 39 | 31.5 | 22.5 |
| Balance (OH$^-$—H$^+$) mmol | 20.77 | 5.78 | −2.40 |
| Average duodenal pH | 6.62 | 6.29 | 6.10 |

Figure 2A:
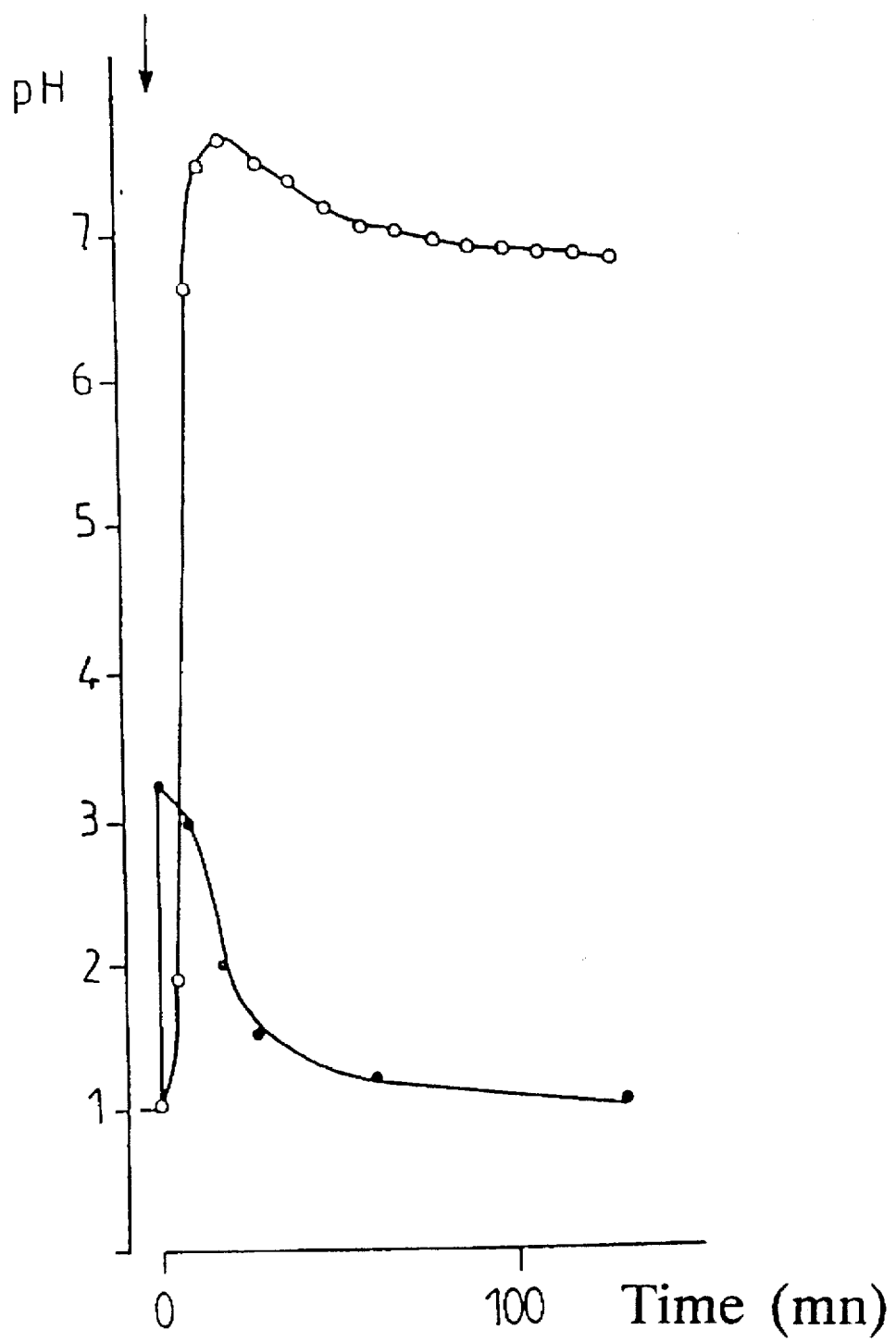
FIG. 2 represents changes of pH over time with a combination of magnesium oxide and guar gum..
Figure 2B:
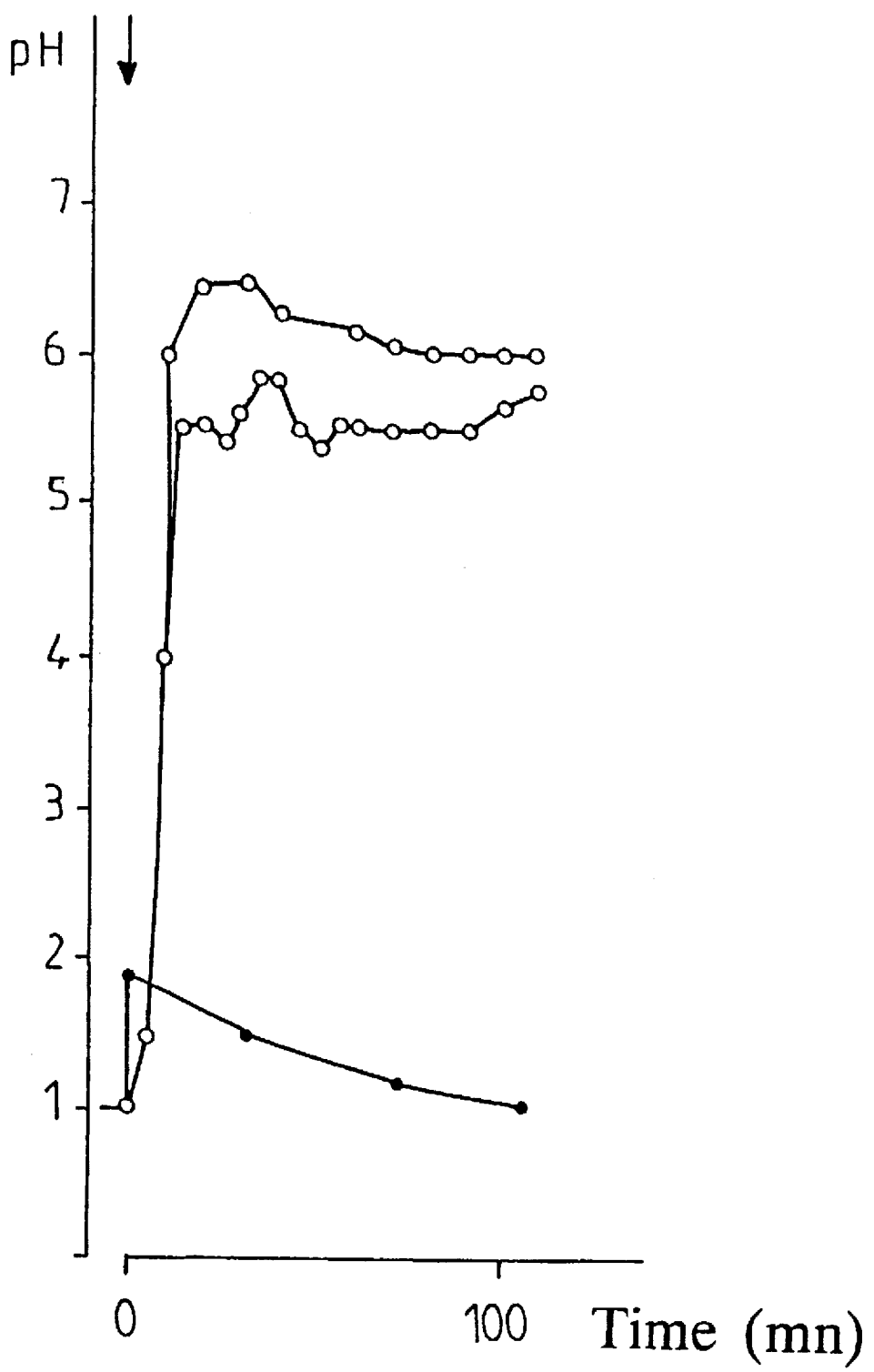
Figure 2C:
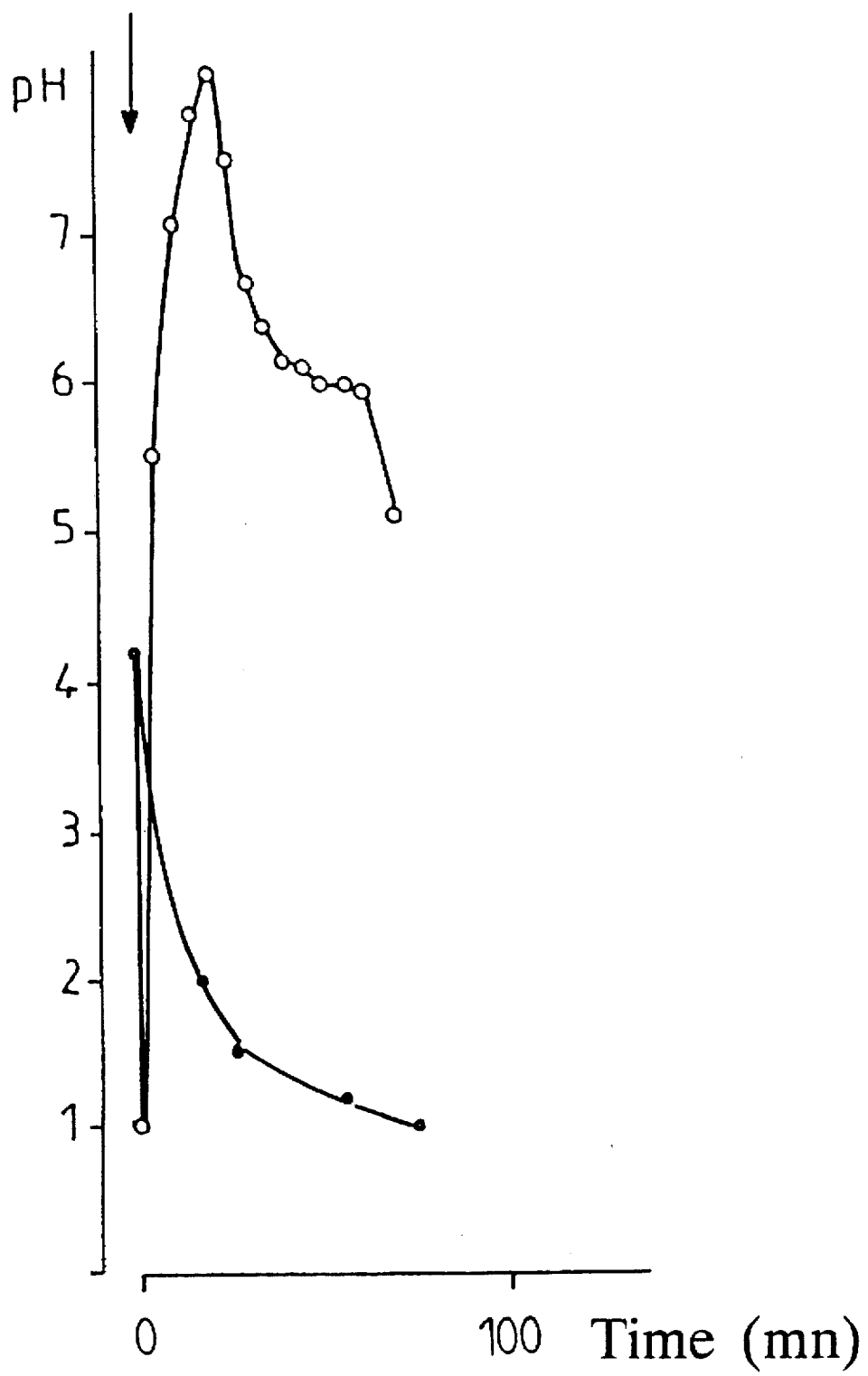

The tracings obtained by the pH meters are reproduced in FIG. 2.

A relationship exists between the quantity of acid used to reach pH 1.0 and the ratio between the secretion and draining flows:

$Y=11.70+26.9$ (R=0.953)

where Y represents the quantity of acid used and x represents the ratio between the secretion and draining flows (3/1.5=2/3.3=1 and 3/4.5=0.66).

The average duodenal pH is closely connected to the balance between alkaline secretion and acid charge.

$Y=0.022 x+6.15$ (r=1.000) where Y represents the duodenal pH and x represents the balance OH$^-$—H$^+$. It appears that, for a value of zero for this balance, the duodenal pH is equal to 6.15.

MGO GOM 001

The results of this test appear in Table II.

TABLE II

| Flow of gastric draining (ml/min) | 1.5 | 3.0 | 4.5 |
|---|---|---|---|
| Gastric environment | | | |
| maximum pH | 8.7 | 7.1 | 8.9 |
| Time (min) to reach pH 1,0 | 260 | 225 | 75 |
| Millimoles of acid used to reach pH 1,0 | 88 | 77.5 | 32.5 |
| Duodenal environment | | | |
| Acid charge in the duodenum (mmol) | 28.65 | 53.38 | 28.77 |
| "Alkaline secretion" mmol | 78 | 67.5 | 22.5 |
| Balance (OH$^-$—H$^+$) mmol | 49.35 | 9.12 | 3.73 |
| Average duodenal pH | 7.13 | 6.70 | 6.61 |

Figure 4A:
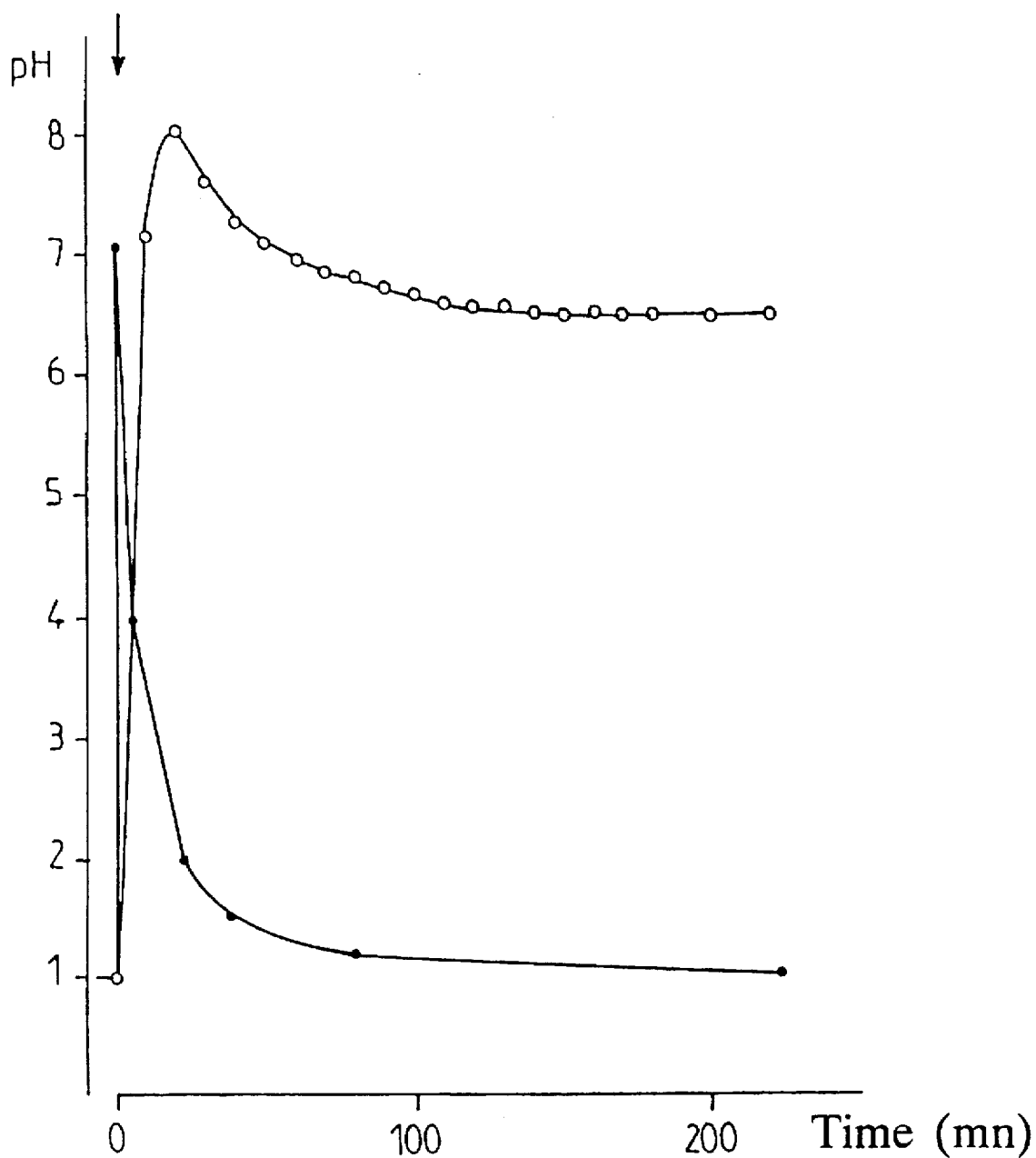
FIG. 4 shows a combination of magnesium oxide an guar gum affecting pH with an emptying time of 3.0 and 4.5 ml/minute.
Figure 4B:
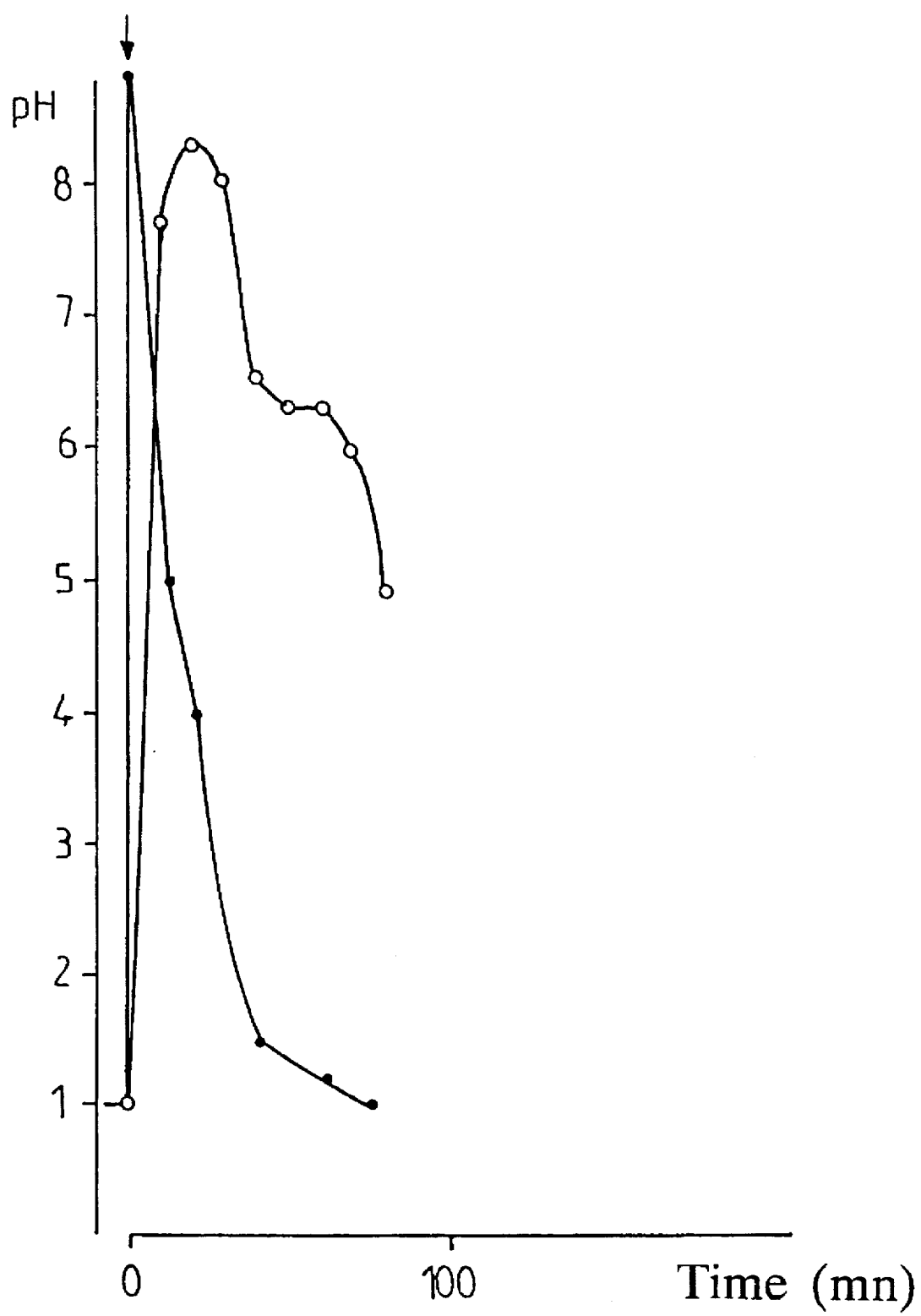

The tracings obtained by the pH meters are reproduced in FIGS. 3 and 4.

The ratio between antacid capacity and the ratio between the secretion and draining flows is calculated as follows:

$Y=34.4+24$ (R=0.812)

The relation between the average duodenal pH and the OH$^-$—H$^+$ balance was calculated as follows:

$Y=0.011x+6.58$ (r=0.998)

For a balance of value zero, the average duodenal pH was equal to 6.58.

MGOH GOM 002

Results of this test appear in Table III.

TABLE III

| Flow of gastric draining (ml/min) | 1.5 | 3.0 | 4.5 |
|---|---|---|---|
| Gastric environment | | | |
| maximum pH | 2.49 | 3.0 | 1.80 |
| Time (min) to reach pH 1,0 | 194 | 109 | 60 |
| Millimoles of acid used to reach pH 1,0 | 68.2 | 42.7 | 28 |
| Duodenal environment | | | |
| Acid charge in the duodenum (mmol) | 27.89 | 28.32 | 24.3 |
| "Alkaline secretion" mmol | 58.2 | 32.7 | 18 |
| Balance (OH$^-$—H$^+$) mmol | 30.31 | 4.38 | −6.30 |
| Average duodenal pH | 6.22 | 5.73 | 5.68 |

Figure 5:
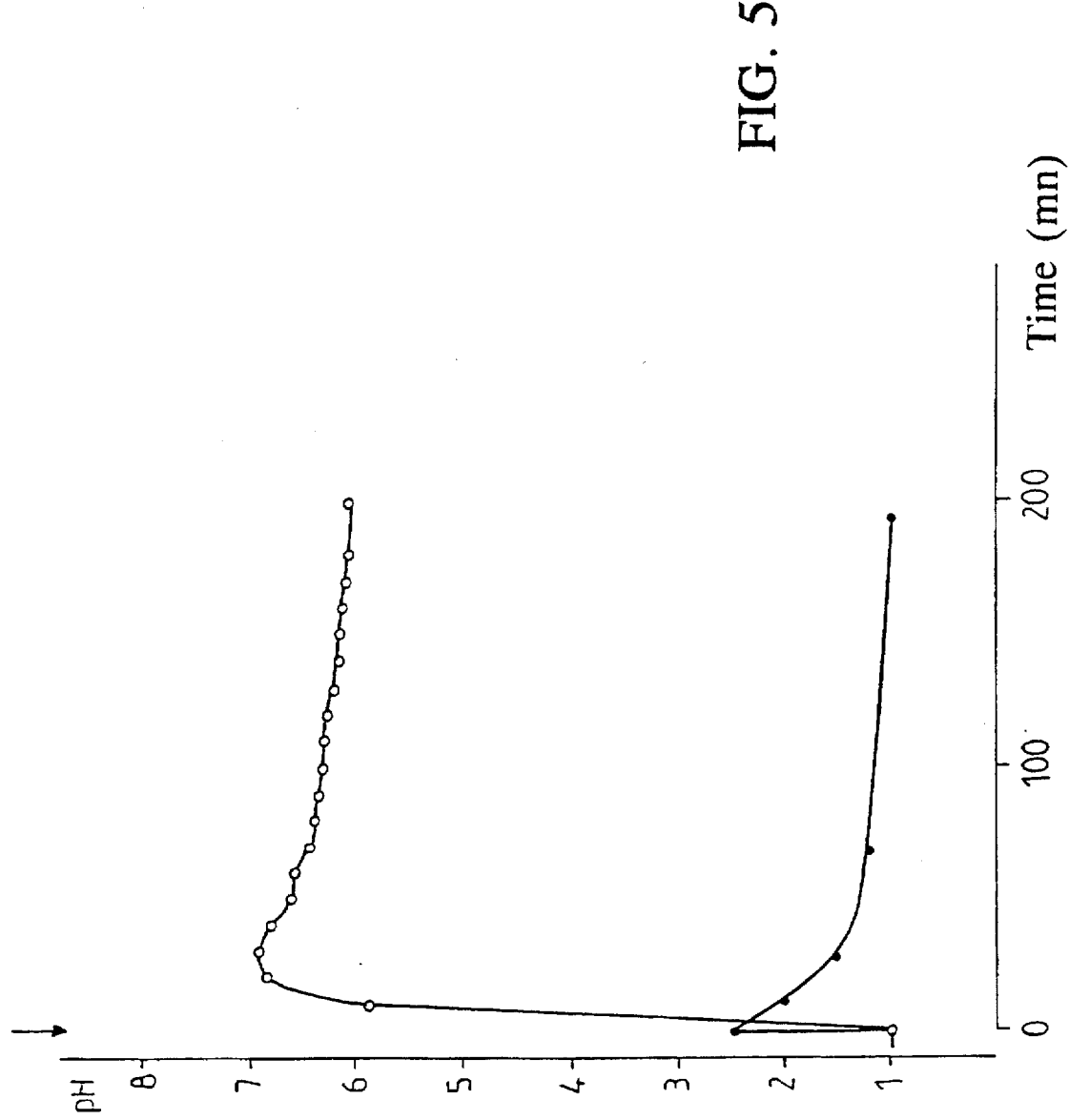
FIG. 5 shows another combination of magnesium oxide and gum with an emptying time of 1.5 ml/minute.
Figure 6A:
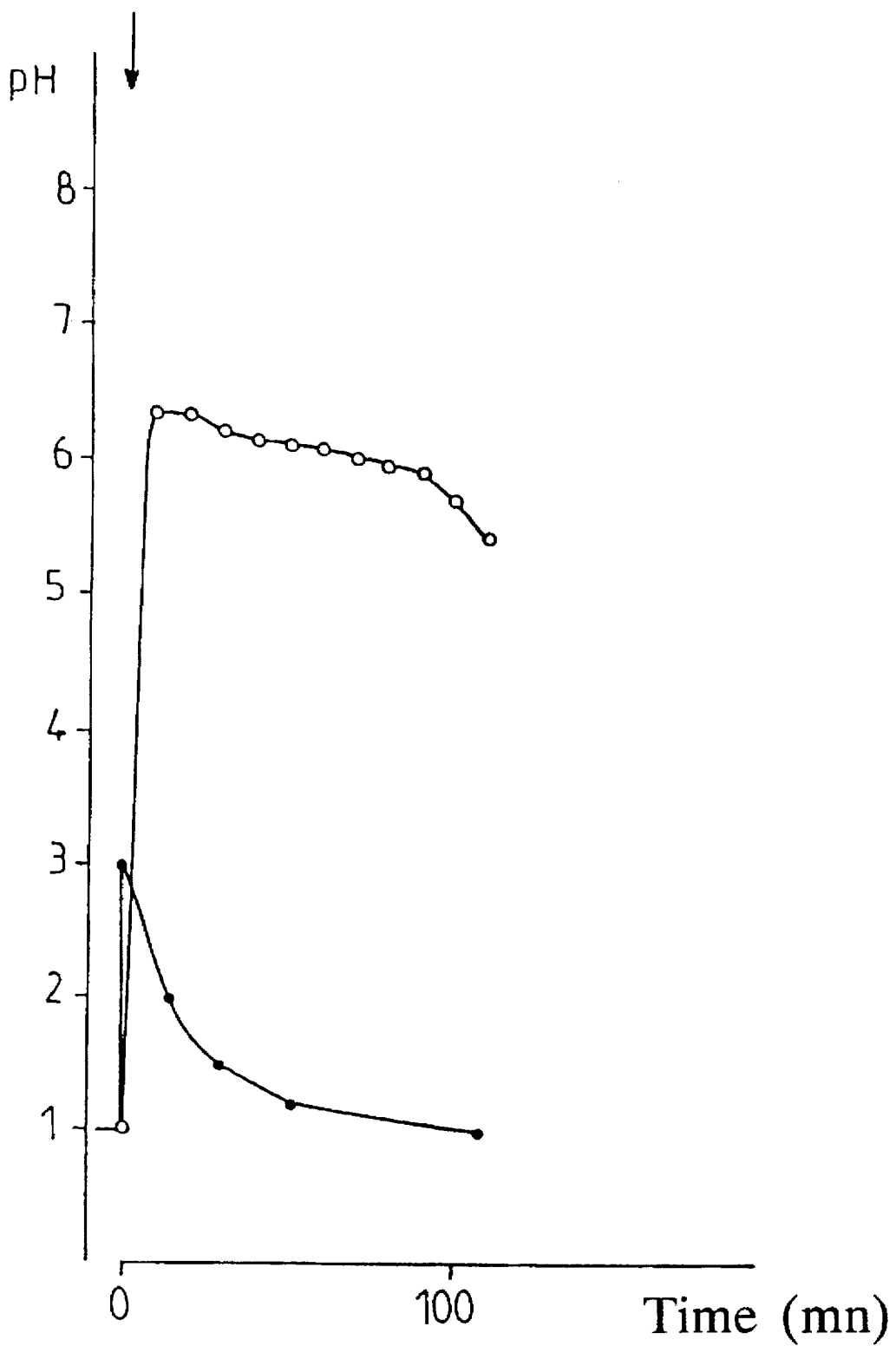
FIG. 6 shows a combination of magnesium oxide and gum with emptying times of 3.0 ml/minute and 4.5 ml/minute.
Figure 6B:
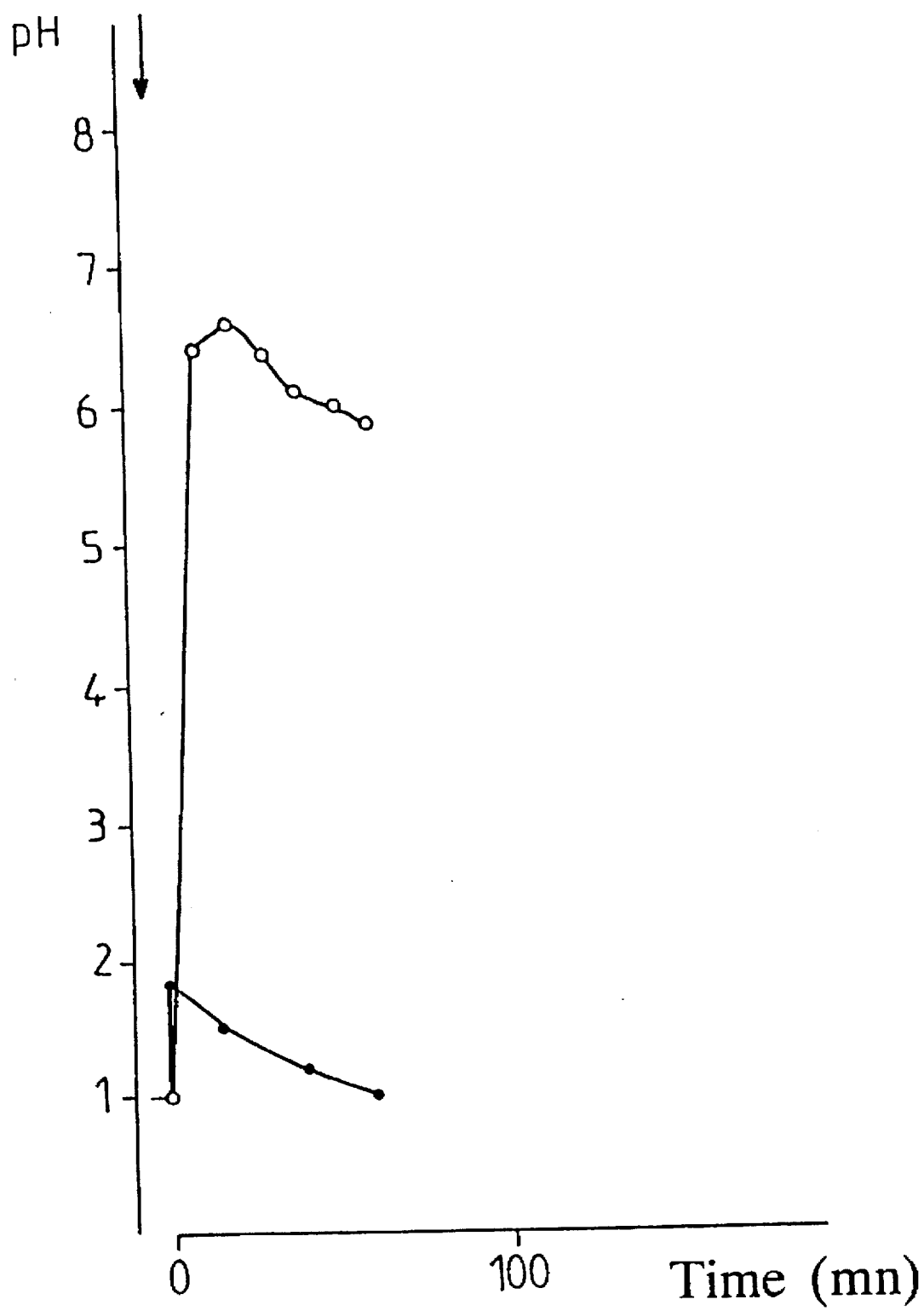
Figure 7:
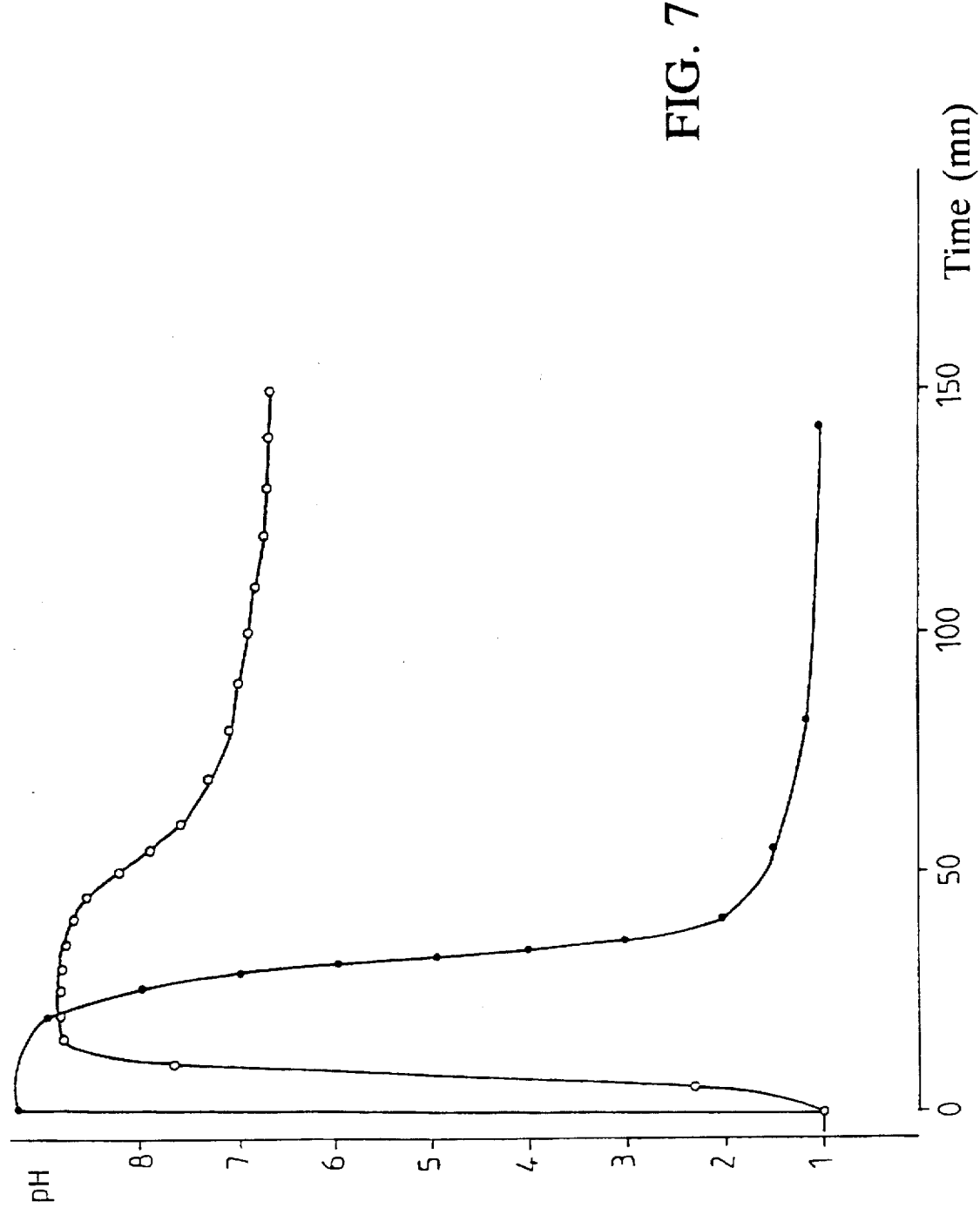
FIG. 7 shows pH changes with magnesium hydroxide with an emptying time of 1.5 ml/minute.
Figure 8A:
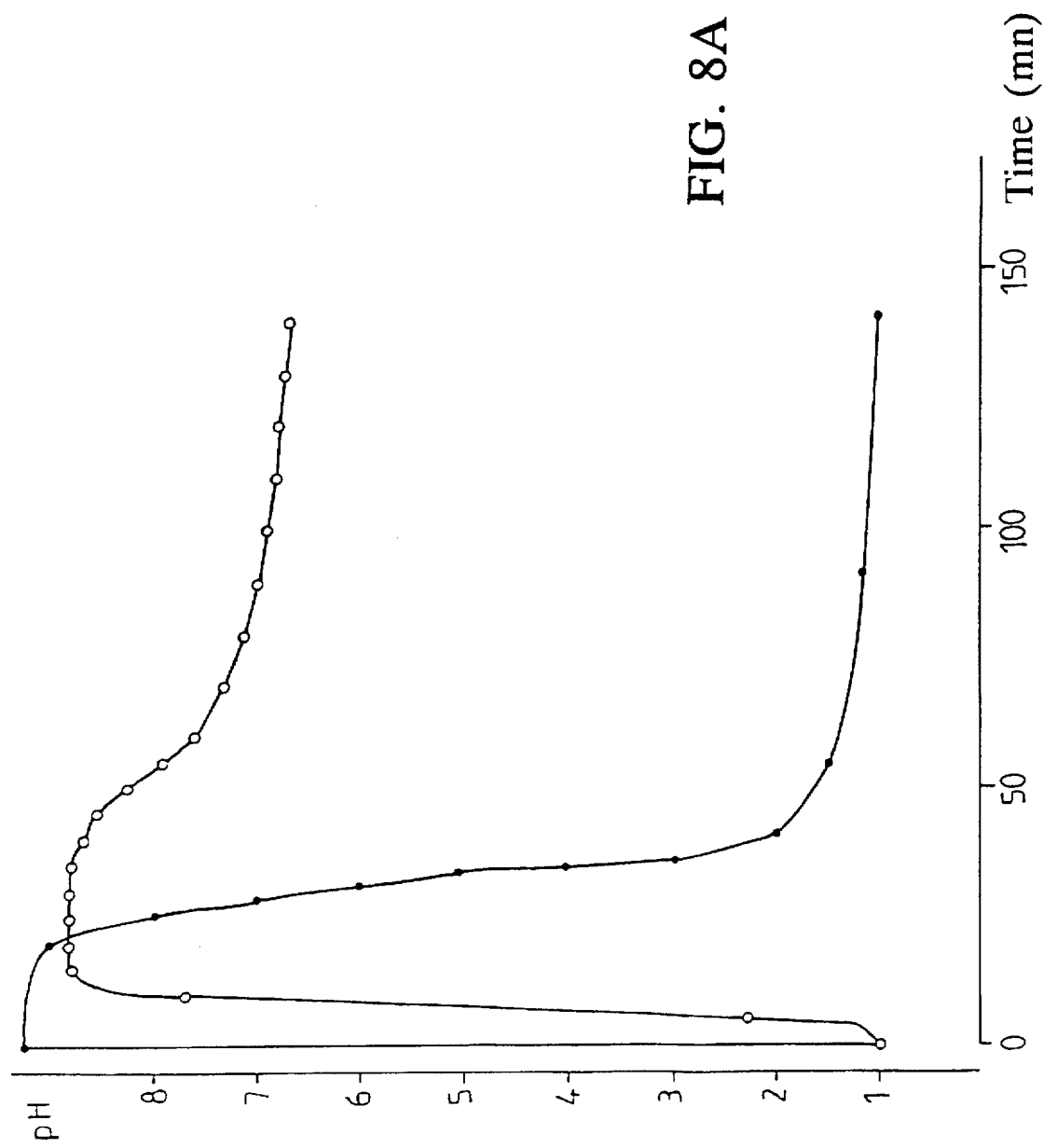
FIG. 8 shows magnesium hydroxide with an emptying time of 3.0 and 4.5 ml/minute.
Figure 8B:
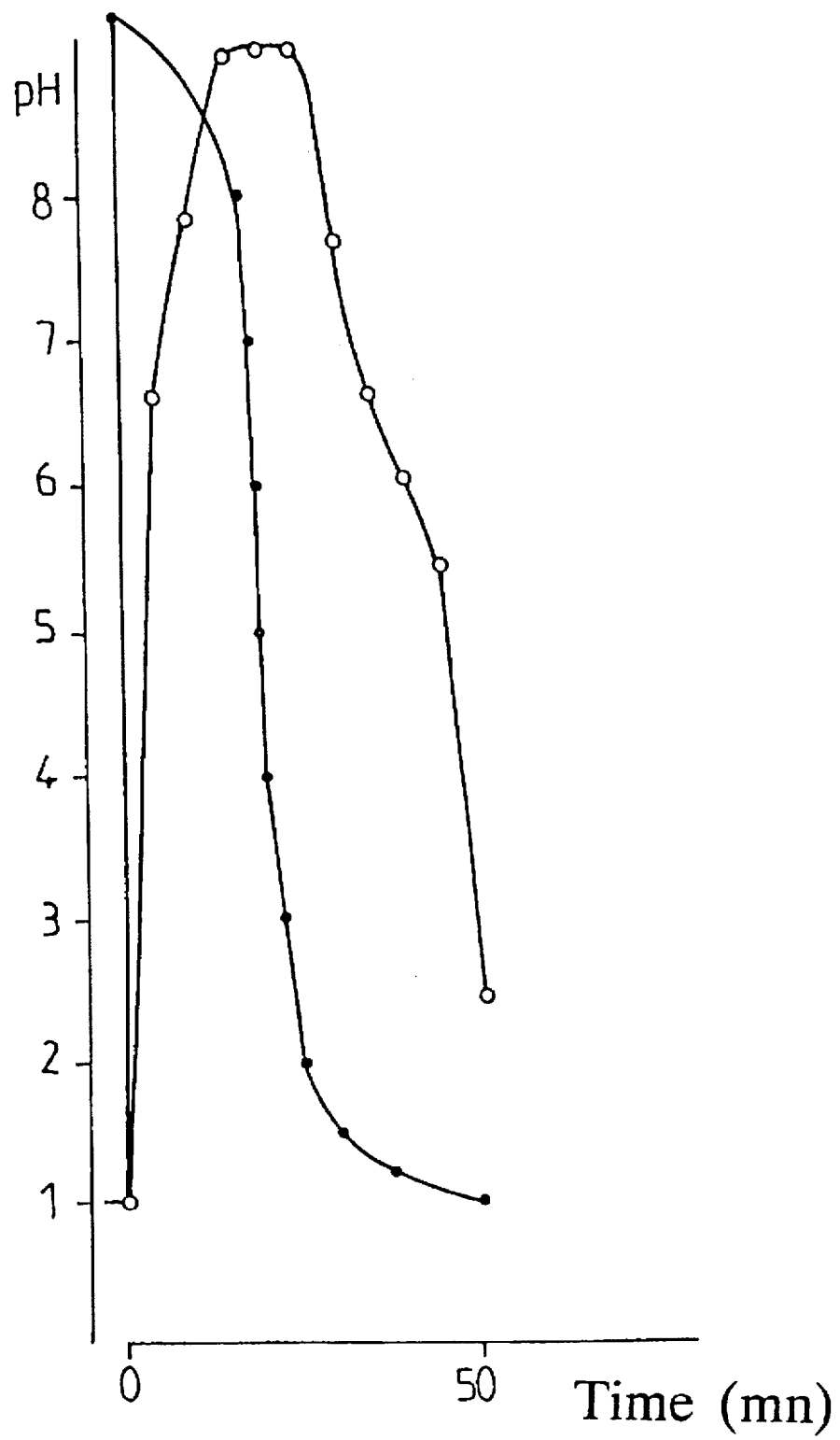

The tracings obtained by the pH meters are reproduced in FIGS. 5 and 6.

The relation between the antacid capacity and the ratio between the secretion and draining flows was calculated as followed:

$Y=80.7x-25$ (r=0.779)

The relation between the average duodenal pH and the OH$^-$—H$^+$ balance was calculated as follows:

$Y=0.015x+5.72$ (r=0.979)

For a balance of value zero, the average duodenal pH is equal to 5.72.

MAGNESIUM HYDROXIDE: 0.8 GRAM

A comparison was made with magnesium salt and uncoated guar gum. The results of this test are shown in Table IV.

TABLE IV

| Flow of gastric draining (ml/min) | 1.5 | 3.0 | 4.5 |
|---|---|---|---|
| Gastric environment | | | |
| maximum pH | 9.6 | 9.5 | 9.3 |
| Time (min) to reach pH 1,0 | 141 | 69 | 50 |
| Millimoles of acid used to reach pH 1,0 | 52.3 | 30.7 | 25 |
| Duodenal environment | | | |
| Acid charge in the duodenum (mmol) | 16.3 | 14.16 | 12.44 |
| "Alkaline secretion" mmol | 42.3 | 20.7 | 15 |
| Balance (OH$^-$—H$^+$) mmol | 26.17 | 6.54 | 2.51 |
| Average duodenal pH | 7.19 | 6.98 | 6.52 |

The relations between the quantity of acid used and the ratio of the secretion and draining flows was calculated as follows:

$Y=20.65+10.80$ (r=0.948)

The relation between the average duodenal pH and the OH$^-$—H$^+$ balance was calculated as follows:

$Y=0.022x+6.63$ (r=0.838)

As can clearly be seen from the above, the combination of magnesium hydroxide and guar gum was not nearly as effective in controlling pH over a period of time as was the combination of antacid salts and coated guar gum according to the present invention.

A comparison of the calculated equations from the correlations between the quantity of acid used and the ratio of secretion and draining flows, in which the slope measures the antacid activity, shows the relative efficiency of the tested preparations:

| MGO GUM 001 | 11.70 |
| MGO GOM 001 | 34.40 |
| MGOH GOM 002 | 80.70 |
| MAGNESIUM HYDROXIDE | 20.65 |

This clearly demonstrates that the greatest antacid activity is exhibited by MGOH GOM 002, which is simultaneously represented by the longer delays to revert to pH 1.0 as compared to magnesium hydroxide and MGO GUM 001. Nevertheless, the delays are inferior to those induced by MGO GOM 001, which shows that producing a larger quantity of acid leads only to a weaker antacid power, this activity being paradoxically not dependent on gastric intraluminal flows.

Intragastric pH rises are moderated with MGOH GOM 002, between 2.5 and 4.5, as well as with MGO GUAR 001, even though it was much more important with magnesium hydroxide and MGO GOM 001, reaching, respectively, 9.5 and 8.0. However, raising the gastric pH to such a high level can in vivo induce liberation of gastrin and cause a secretory acid rebound, which would not be the case with MGOH GOM 002 and MGO GUM 001.

It was found that simethicone-coated guar gum combined with a dose of magnesium oxide or magnesium hydroxide of 0.5 grams changes the behaviors of magnesium salts in altering gastric pH and in delaying the effect on neutralization such that it takes longer to reach a pH of 1.0. This corresponds to a much more powerful and longer-lasting antacid activity, which is particularly evident with MGOH GOM 002.

In the duodenal environment, one can observe a narrow dependence between the average pH of the duodenal content and the balance between the alkaline secretion and the acid charge which penetrates into the duodenum, i.e., the $OH^-$—$H^+$ balance. A high value for the average duodenal pH corresponds to a saving of bicarbonates secreted by a neutralizing antacid effect in a gastric environment. This value of the duodenal pH can be evaluated by the value of the pH when the balance $OH^-$—$H^+$ has a value of zero.

These values for the compositions tested are:

| MGO GUM | 6.15 |
| MGO GOM 001 | 6.58 |
| MGO GOM 002 | 5.72 |
| MAGNESIUM HYDROXIDE | 6.63 |

As can be seen from the above, the saving of bicarbonates is most important with magnesium hydroxide, and decreases with MGO GOM 001, MGO GUM 001, and MGOH GOM 002, in which the value of 5.72 corresponds to a physiological value of the duodenal pH in vivo.

The three preparations based upon the present invention have demonstrated that in a gastric environment they exert a strong antacid activity, and that in a duodenal environment they induce an average duodenal pH in accordance with physiological values. These are the criteria desired in an antacid.

The association of simethicone-coated gum with conventional antacid salts provides antacids which do not raise the gastric pH to dangerously high levels, while they are strong in acid absorption and do not modify the physiological conditions of the duodenal pH. This combination of simethicone-coated guar gum with conventional antacid salts provides long-lasting relief of excess acid production while avoiding the problem of acid rebound previously associated with many antacid salts.

In another study, the antacid capacity of an antacid suspension added to the guar gum coated with simethicone gives an action time of greater than five hours.

The present invention enables the use of magnesium and calcium rather than solely aluminum for treating stomach acidity. When calcium carbonate is used as the antacid, the simethicone is useful for its antifoaming properties as well.

When an antacid composition according to the present invention is ingested, the hydrochloric acid in the stomach converts the alkaline antacid salt to a chloride salt, e.g., magnesium hydroxide to magnesium chloride, or calcium carbonate to calcium chloride. This chloride salt has an antacid capacity which does not disturb the acid balance in the digestive system. When magnesium or calcium salts are used as the antacid salts, they can also be used for magnesium or calcium therapy without disturbing the acid balance of the digestive system. By delivering the cation of interest, i.e., magnesium or calcium, over a long period of time with no disturbance of the acid balance, the patient is better to absorb the cation of interest, and better cellular penetration of the cation of interest is obtained.

The compositions of the present invention, i.e., pharmaceutically acceptable gum coated with simethicone combined with a physiological antacid or mineralizing salt, exhibit prolonged activity and can also include other compatible therapeutic substances. For example, a fluorine salt, such as sodium monofluorophosphate, to reduce incidence of cavities, can be added to calcium carbonate. Likewise, aspirin or acetaminophen, can be added to the combination of coated gum and antacid salt. These active ingredients can be added in amounts of up to about 2 grams per dose, depending upon the amount of active ingredient it is desired to administer at one time.

Examples of compositions according to the present invention which includes another therapeutic are as follows:

EXAMPLE 1

| coated guar-gum | 1 gram |
| magnesium hydroxide | 0.5 gram |
| aspirin | 0.5 gram |

EXAMPLE 2

| coated guar gum | 1 gram |
| calcium carbonate | 1 gram |
| sodium monofluorophosphate | 100 mg |

In the case of the additional ingredients, such as aspirin or sodium monofluorophosphate, the therapeutic is slowly released and is slowly diffused through the intestinal tract to provide prolonged release of the active ingredients.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A pharmaceutical antacid composition comprising:
   (a) a pharmaceutically acceptable gum which forms a viscous suspension with water which suspension is viscous enough to adhere to the oesogastroduodenal lining; said gum being coated with simethicone;
   (b) an antacid salt.

2. The pharmaceutical antacid composition according to claim 1 wherein the gum is guar gum.

3. The pharmaceutical antacid composition according to claim 1 wherein the antacid salt is selected from pharmaceutically acceptable salts of magnesium and calcium.

4. The pharmaceutical antacid composition according to claim 1 further including a compatible therapeutically active substance.

5. The pharmaceutical antacid composition according to claim 1 wherein said compatible therapeutically active substance is selected from the group consisting of analgesics; gold salts; fluorine derivatives; anticoagulants; and antibiotics.

6. A method for treating excess gastrointestinal acidity comprising the step of administering a pharmaceutical antacid composition comprising a therapeutically effective amount of a pharmaceutical antacid composition according to claim 1.

7. The pharmaceutical antacid composition according to claim 1 wherein the ratio of simethicone is from about 10:1 to about 1:10 by weight of the composition.

* * * * *

UNITED STATES PATENT AND TRADEMARK OFFICE
CERTIFICATE OF CORRECTION

PATENT NO. : 5,667,802
DATED : September 16, 1997
INVENTOR(S) : Georges Serge Grimberg It is certified that error appears in the above-identified patent and that said Letters Patent is hereby corrected as shown below:

Title page, item [76], inventor: address should read--123 instead of 127--.

Column 5, line 49, delete "28.77" and insert therefor--18.77--.

Signed and Sealed this

Twenty-third Day of December, 1997

Attest:

BRUCE LEHMAN

*Attesting Officer*  *Commissioner of Patents and Trademarks*